United States Patent
Pastore

(10) Patent No.: US 8,374,498 B2
(45) Date of Patent: *Feb. 12, 2013

(54) SYSTEMS AND/OR DEVICES FOR CAMERA-BASED INSPECTIONS

(75) Inventor: Timothy M Pastore, Wakefield, MA (US)

(73) Assignee: Microscan Systems, Inc., Renton, WA (US)

( * ) Notice: Subject to any disclaimer, the term of this patent is extended or adjusted under 35 U.S.C. 154(b) by 444 days.

This patent is subject to a terminal disclaimer.

(21) Appl. No.: 11/904,229

(22) Filed: Sep. 26, 2007

(65) Prior Publication Data

US 2008/0170380 A1 Jul. 17, 2008

Related U.S. Application Data

(60) Provisional application No. 60/848,311, filed on Sep. 29, 2006.

(51) Int. Cl.
| G03B 15/06 | (2006.01) |
| G03B 17/00 | (2006.01) |
| G03B 11/00 | (2006.01) |
| G02B 6/00 | (2006.01) |
| G02B 7/02 | (2006.01) |
| G05D 25/00 | (2006.01) |
| H04N 5/222 | (2006.01) |

(52) U.S. Cl. ........ 396/199; 396/267; 396/544; 348/370; 362/16; 362/551; 362/552; 362/558

(58) Field of Classification Search ................ 396/155, 396/199, 267, 544; 348/370; 362/16, 551, 362/555, 558

See application file for complete search history.

(56) References Cited

U.S. PATENT DOCUMENTS

| 3,614,449 A | 10/1971 | Ward, III |
| 4,099,221 A | 7/1978 | Carrillo |
| 4,594,645 A | 6/1986 | Terashita |
| 4,653,875 A | 3/1987 | Hines |
| 5,172,005 A | 12/1992 | Cochran et al. |
| 5,408,084 A | 4/1995 | Brandorff et al. |
| 5,461,417 A | 10/1995 | White et al. |
| 5,539,485 A | 7/1996 | White |
| 5,604,550 A | 2/1997 | White |
| 5,619,029 A | 4/1997 | Roxby et al. |
| 5,684,530 A | 11/1997 | White |
| 5,761,540 A | 6/1998 | White |
| 5,859,418 A | 1/1999 | Li et al. |
| 5,903,394 A | 5/1999 | Sipotz, Jr. |
| 5,999,751 A | 12/1999 | Imamura et al. |
| 6,052,534 A | 4/2000 | Goto |

(Continued)

FOREIGN PATENT DOCUMENTS

| EP | 0 685 140 B1 | 12/1995 |
| EP | 1455179 A1 | 9/2004 |

(Continued)

OTHER PUBLICATIONS

International Search Report PCT/US2007/021064, mail date May 15, 2008.

(Continued)

*Primary Examiner* — Rochelle-Ann J Blackman
(74) *Attorney, Agent, or Firm* — Blakely Sokoloff Taylor & Zafman LLP

(57) ABSTRACT

Certain exemplary embodiments can provide a system comprising: a diffuser defining a camera lens hole in a top portion of said diffuser, said diffuser adapted to receive at least one set of low angle lights; and a plurality of lights mounted on said diffuser in proximity to said camera lens hole.

34 Claims, 6 Drawing Sheets

U.S. PATENT DOCUMENTS

| | | |
|---|---|---|
| 6,247,645 B1 | 6/2001 | Harris et al. |
| 6,324,024 B1 | 11/2001 | Shirai et al. |
| 6,552,783 B1 | 4/2003 | Schmidt et al. |
| 7,198,384 B2 | 4/2007 | Kakiuchi et al. |
| 7,783,178 B2 | 8/2010 | Liu |
| 7,877,003 B2 | 1/2011 | Dunn et al. |
| 7,978,970 B2 | 7/2011 | Pastore |
| 8,000,594 B2 | 8/2011 | Messina |
| 8,032,017 B2 | 10/2011 | Pastore |
| 8,107,808 B2 | 1/2012 | Messina et al. |
| 2001/0026320 A1 | 10/2001 | Seo |
| 2004/0001344 A1 | 1/2004 | Hecht |
| 2005/0030960 A1 | 2/2005 | Sumida et al. |
| 2005/0237423 A1 | 10/2005 | Nilson et al. |
| 2007/0090193 A1 | 4/2007 | Nunnink et al. |
| 2008/0106794 A1 | 5/2008 | Messina |
| 2008/0137323 A1 | 6/2008 | Pastore |
| 2008/0137324 A1 | 6/2008 | Pastore |
| 2008/0137325 A1 | 6/2008 | Pastore |
| 2008/0158854 A1 | 7/2008 | Matsui |
| 2009/0003810 A1 | 1/2009 | Dunn et al. |
| 2011/0002682 A1 | 1/2011 | Messina |
| 2011/0008035 A1 | 1/2011 | Messina et al. |
| 2012/0002957 A1 | 1/2012 | Pastore |
| 2012/0121245 A1 | 5/2012 | Messina et al. |

FOREIGN PATENT DOCUMENTS

| | | |
|---|---|---|
| EP | 1688861 A2 | 8/2006 |
| WO | WO 9922224 | 5/1999 |
| WO | WO 99/40361 A1 | 8/1999 |
| WO | WO 02/075637 A1 | 9/2002 |
| WO | WO 2005/043449 A1 | 5/2005 |
| WO | WO/2008/039541 A2 | 4/2008 |

OTHER PUBLICATIONS

PCT Written Opinion of the International Searching Authority PCT/US2007/021064, mail date May 15, 2008.

U.S. Notice of Allowance mailed Apr. 28, 2011, U.S. Appl. No. 11/904,240, filed Sep. 26, 2007 (12 pages).

U.S. Notice of Allowance mailed May 26, 2011, U.S. Appl. No. 11/904,241, filed Sep. 26, 2007 (18 pages).

AIM Global Document: AIM DPM-1-2006, "Direct Part Mark (DPM) Quality Guideline", AIM Bar Code Guideline, Version 1.0, Dec. 12, 2006, 20 pages.

PCT/US2008/007673, International Search Report and Written Opinion of the International Searching Authority, mail date Oct. 13, 2008, 11 pages.

U.S. Office Action mailed Feb. 3, 2010, U.S. Appl. No. 11/904,259, filed Sep. 26, 2007 (17 pages).

U.S. Office Action mailed Feb. 12, 2010, U.S. Appl. No. 11/904,241, filed Sep. 26, 2007 (18 pages).

U.S. Office Action mailed Jul. 14, 2010, U.S. Appl. No. 11/904,241, filed Sep. 26, 2007 (10 pages).

U.S. Office Action mailed Nov. 10, 2010, U.S. Appl. No. 11/904,240, filed Sep. 26, 2007 (16 pages).

U.S. Office Action mailed Nov. 10, 2010, U.S. Appl. No. 11/904,241, filed Sep. 26, 2007 (18 pages).

Examination Report for European Patent Application No. EP 07 839 090.3, dated Oct. 22, 2009 (3 pages).

Examination Report for European Patent Application No. EP 07 839 090.3, dated Sep. 21, 2010 (6 pages).

Examination Report for European Patent Application No. EP 07 839 090.3, dated Mar. 19, 2012 (5 pages).

U.S. Office Action mailed Apr. 13, 2012, U.S. Appl. No. 13/233,535, filed Sep. 15, 2011 (25 pages).

U.S. Notice of Allowance mailed May 24, 2012, U.S. Appl. No. 13/233,535, filed Sep. 15, 2011 (11 pages).

SYSTEMS AND/OR DEVICES FOR CAMERA-BASED INSPECTIONS

CROSS-REFERENCES TO RELATED APPLICATIONS

This application claims priority to, and incorporates by reference herein in its entirety, pending U.S. Provisional Patent Application Ser. No. 60/848,311, filed 29 Sep. 2006.

BACKGROUND

Camera-based inspections often require lighting to be optimized for a given application. Optimized lighting for an application can become difficult when parts vary in geometry and/or finish.

Direct Part Marking (DPM) is a technology whereby an item is physically altered by methods such as dot peening, laser etching, molding, and/or embossing to produce two different surface conditions.

Marking can result in the symbol being created by either smooth and rough (or dull and shiny) areas on the substrate or a symbol comprised "dots" below or above the substrate surface. DPM is typically used with matrix symbologies.

As a result, there is often very little or no contrast between the "marked" elements of a symbol and the background (substrate). Contrast can be achieved by using specific types of lighting and signal processing techniques.

A Data Matrix is a type of barcode that relies on print quality grading systems to ensure that the codes are printed well and will be readable in the future. The Association for Automatic Identification and Mobility (AIM) maintains a specification for Data Matrix verification, which is a process of determining the print quality of, for example, a "barcode", a symbol created by Direct Part Marking, etc. Using the traditional barcode as an example, let's say that you were printing the barcode and the toner on your printer was running low, such that you have a section where the barcode is faded and/or missing some of the bars. You also might have an overzealous courier who makes a black line with a marker through the barcode. These types of damage to the code can make it difficult or impossible to read the barcode. The same principle exists for 3D barcodes. For example, if a laser is marking a fuel injector and the beam passes over a drop of oil, it might not mark the part in that section. The specification mentioned above has a series of tests for issues such as missing parts of the code, faded codes, and angular distorted codes. If you were to put a mark on a mirror surface or a flat black cylinder, if you do not utilize the right light, you might not even see the mark. The following text is the summary of the AIM specification's currently required lighting:

Lighting

Two lighting environments each with sub-options are defined in this document. The lighting environments are denoted in the reported grade using the format defined in ISO/IEC 15415, section 6.2, using the angle specifier with a combination of numbers and letters as defined below.

Note: This does not limit the prerogative of an Application Specification to choose different lighting environments based on application requirements. Alternate lighting environments should include specifiers consistent with the format of those below that can be used for communicating quality requirements and quality grades.

Diffuse Lighting

Diffuse Perpendicular (On-axis/Bright Field) (90)

A flat diffusing material is oriented such that the plane of the material is parallel to the plane of the sensor. The symbol is uniformly illuminated with diffuse light incident at 90 degrees to the plane of the symbol. The angle specifier shall be 90.

Diffuse Off-axis (D)

A diffusely reflecting dome is illuminated from below so that the reflected light falls non-directionally on the part and does not cast defined shadows. This is commonly used for reading curved parts. The angle specifier shall be D.

Directional Lighting

Two orthogonal lighting planes are defined such that both planes are perpendicular to the surface of the image sensor and one plane is parallel to the line formed by a horizontal edge of the image sensor to within +/−5 degrees. Light is directionally aimed at the part such that the line formed by the center of the light source and center of the symbol rests in one of the lighting planes and is at an angle of 30+/−3 degrees from the horizontal plane of the surface of the symbol. The lighting shall illuminate the entire symbol area with uniform energy.

Low Angle, Four Direction (30Q)

Light is aimed at the part from four sides. The angle specifier shall be 30Q.

Low Angle, Two Direction (30T)

Light is aimed at the part from two sides in one of the two lighting planes. The angle specifier shall be 30T.

Low Angle, One Direction (30S)

Light is aimed at the part from any one of the four sides. The angle specifier shall be 30S.

Thus, conventional technology can require a user to manually change the lighting used for each of a number of different verification methods.

SUMMARY

Combining a number of different lighting techniques into one single system to enable the user and/or a user program to cycle through the options until the optimal lighting is selected can be desirable. There can be a substantial utility for a system that provides all of the options required by a specification such as that described supra by AIM (and/or other options for non-Data Matrix Verification applications) without a user having to manually change from one given light to another.

Certain exemplary embodiments can provide a system comprising: a diffuser defining a camera lens hole in a top portion of said diffuser, said diffuser adapted to receive at least one set of low angle lights; and a plurality of lights mounted on said diffuser in proximity to said camera lens hole.

Certain exemplary embodiments can enable the utilization of any of many different lighting techniques via a single system, which can be helpful for camera-based inspections, such as for machine vision applications such as Data Matrix Verification.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

The lighting system of certain exemplary embodiments can independently, programmatically, and/or automatically control any of at least 4 low angle lights. Continuously Diffuse Illumination (CDI) uniformity on the top of the dome can be improved by using illumination from a bright field illumination source, such as LED's. In certain exemplary embodiments, the bright field LEDs can be set to a lower intensity. The low angle lights could be controlled to illuminate one light at a time (e.g., N, S, E, or W), two at a time (e.g., N-S, E-W), and/or all four at a time. The CDI lighting can be only created by the reflection of the upward facing LEDs or could be created by backlighting the translucent dome.

The automatic lighting system of certain exemplary embodiments can be applied to determine compliance with various specifications of the AIM's Technical Symbology Committee and/or to non-Data Matrix machine vision applications.

The AIM TSC lighting combinations can include any of:
Dome lighting
Bright Field Diffuse lighting
Low angle non-diffuse from the North location
Low angle non-diffuse from the South location
Low angle non-diffuse from the East location
Low angle non-diffuse from the West location
Low angle non-diffuse from the North-South locations
Low angle non-diffuse from the East-West locations
Low angle non-diffuse from the North-South-East-West locations Certain exemplary embodiments can fulfill at least the AIM TSC lighting requirements.

Certain exemplary embodiments can provide a method of creating a CDI effect. CDI as described above also has the nickname of "Cloudy Day Illumination", where the "effect" is little or no shadows. To facilitate this effect, certain exemplary embodiments can interpose a diffusion material and/or diffuser between a source of bright field, low angle, and/or indirect, dome lighting elements and the part to be illuminated.

Figure 1:
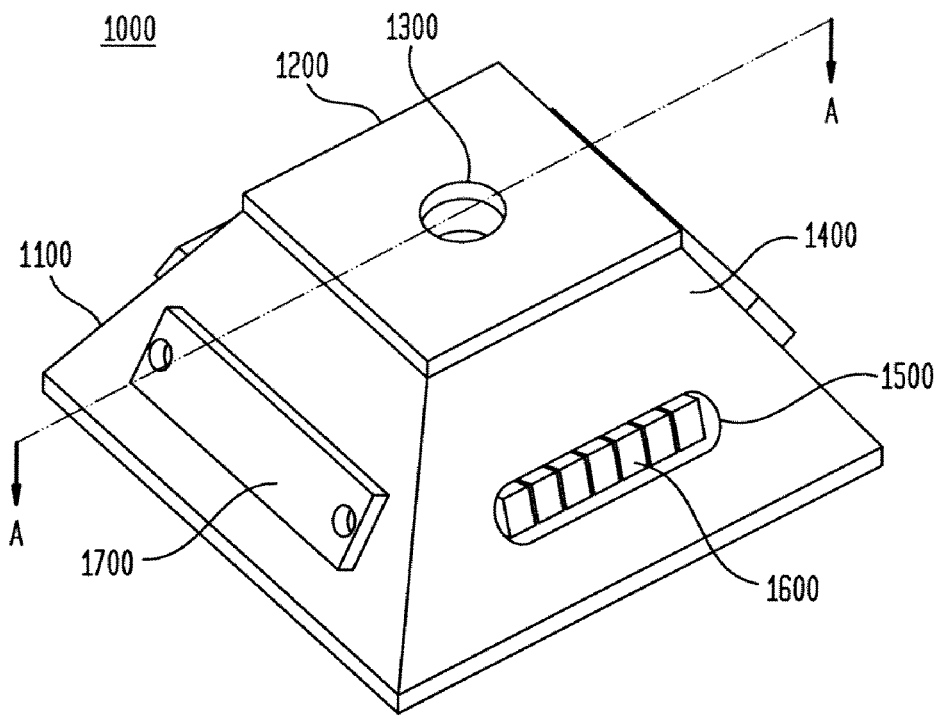
FIG. 1 is a perspective view of an exemplary embodiment of a system 1000.

FIG. 1 is a perspective view of an exemplary embodiment of a system 1000, which can comprise a substantially dome-shaped diffuser 1100, which can be formed in the shape of, for example, a truncated 4-sided pyramid, a truncated circular cone, a truncated right circular cone, etc., and can be formed from a optically translucent diffuser material, such as UHMW and/or Teflon. A top mount 1200 can attach, to diffuser 1100, one or more bright field lights 1250, which can be, for example, Light Emitting Diodes (LED's). When their illumination is diffused by diffuser 1100, bright field lights 1250 can be considered "bright field diffuse lights". Top mount 1200 can define a camera lens hole 1300, through which light can enter a camera lens. One or more side portions 1400 of diffuser 1100 can include one or more thinned portions 1500, which can provide minimal diffusion of light that passes therethrough. Mounted in a thinned portion 1500 on diffuser 1100 can be one or more low angle lights 1600, which can be, for example, Light Emitting Diodes (LED's). A mount 1700 can secure the low angle light 1600 to diffuser 1100. The thinned portion 1500 can allow for a low angle light 1600 to be non-diffuse while also allowing for the diffuser material to act as a mount for the low angle light 1600, illumination from which can penetrate the diffuser, substantially face an interior zone of the diffuser, and/or diffusely illuminate the interior zone of the diffuser.

Figure 2:
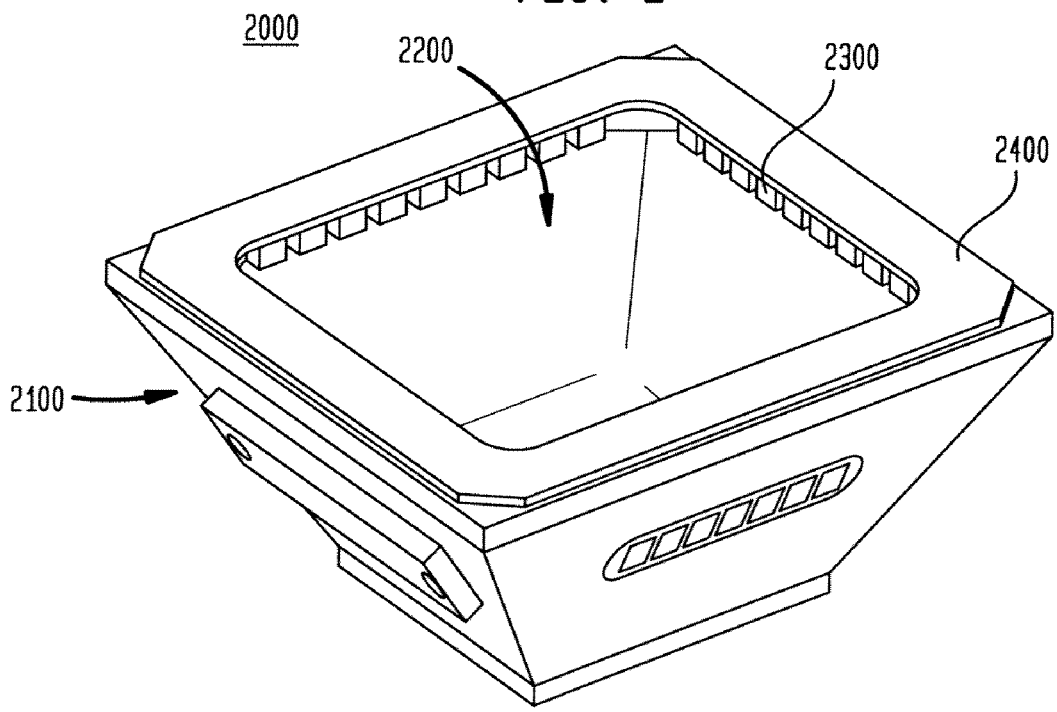
FIG. 2 is a perspective view of an exemplary embodiment of a system 2000.

FIG. 2 is a perspective view of an exemplary embodiment of a system 2000, which can comprise a substantially dome-shaped diffuser 2100, which can be formed in the shape of, for example, a truncated 4-sided pyramid, a truncated circular cone, a truncated right circular cone, etc., and can be formed from a diffuser material. An interior textured surface 2200 of diffuser 2100 can be adapted to face an object to be photographed and/or be illuminated by one or more dome lights 2300, which can be, for example, LED's. Supporting dome lights 2300 can be a dome light mount 2400.

Figure 3:
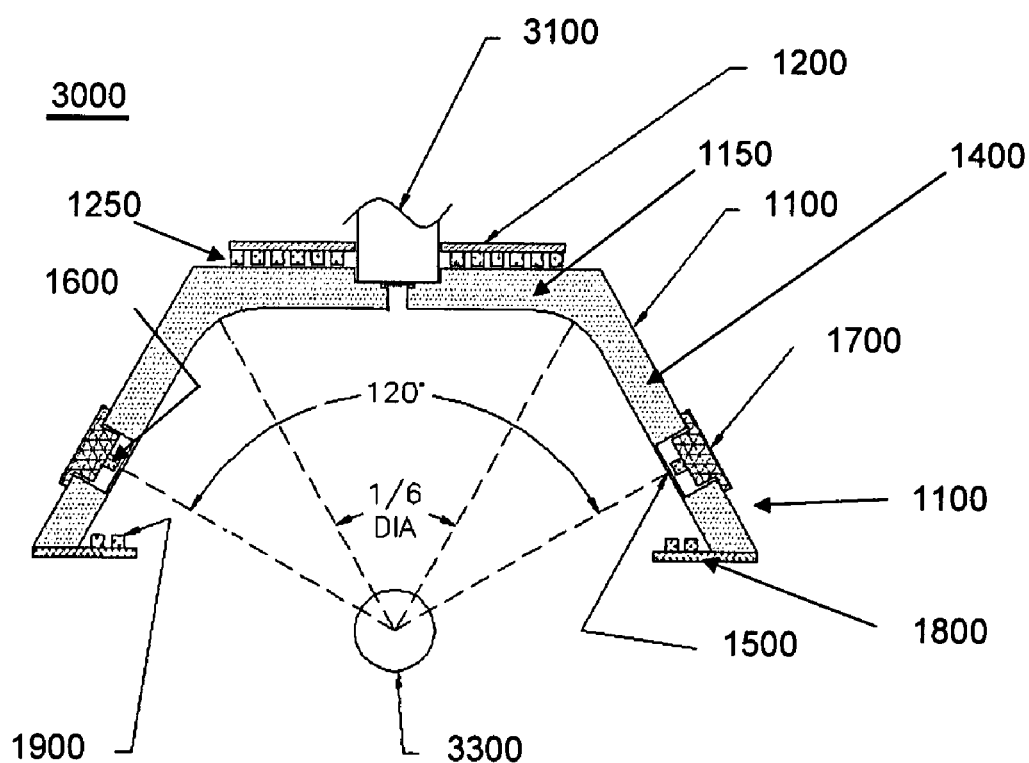
FIG. 3 is a cross-sectional view taken along plane A-A of FIG. 1 of an exemplary embodiment of a system 3000.

FIG. 3 is a cross-sectional view taken along plane A-A of FIG. 1 of an exemplary embodiment of a system 3000, which can be a "three geometry" lighting system and/or which can comprise a substantially dome-shaped diffuser 1100. To a top portion 1150 of diffuser 1100 can be secured a top mount 1200, which can secure to diffuser 1100 one or more bright field lights 1250, which can be, for example, LED's. Mounted co-axially on top mount 1200, through a hole in top mount 1200, and/or within a cavity in top portion 1150 can be a lens 3100 that can be attached to a camera.

Each side portion 1400 of diffuser 1100 can include a thinned portion 1500, which can allow for minimal diffusion of low angle lighting. Securing one or more low angle lights 1600 to side portion 1400 can be a low angle light mount 1700. One or more dome lights 1900 can be adapted to substantially illuminate at least a portion of a textured interior surface of diffuser 1100. Securing one or more dome lights 1900 to diffuser 1100 can be a dome light mount 1800. Any of lights 1250, 1600, or 1900 can be used to illuminate an inspected part 3300.

Arrays of low angle lights 1600 located on opposing side portions 1400 of diffuser 1100 can be separated by, for example, approximately 120 degrees as measured from a cross-sectional axis of an inspected part 3300. Diffuser 1100 can effectively illuminate part 3300 from 3 sides of a substantially hexagonally shaped zone. A rule of thumb for using a camera to look at a cylindrical part is to keep the barcode width less than $\frac{1}{6}^{th}$ the diameter of the cylinder. For example, for a cylindrical part with a 6 inch diameter, the rule of thumb suggests limiting the width of a Data Matrix marked on the part to approximately 1 inch. Top portion 1150 and each of side portions 1400 of diffuser 1100 can be dimensioned and/or positioned to correspond to a projection of that Data Matrix. Thus, system 1000 and/or diffuser 1100 can provide illumination at angles sufficient to meet a plurality of lighting requirements for camera-based inspections of cylindrical parts (and/or other shaped parts).

Figure 4:
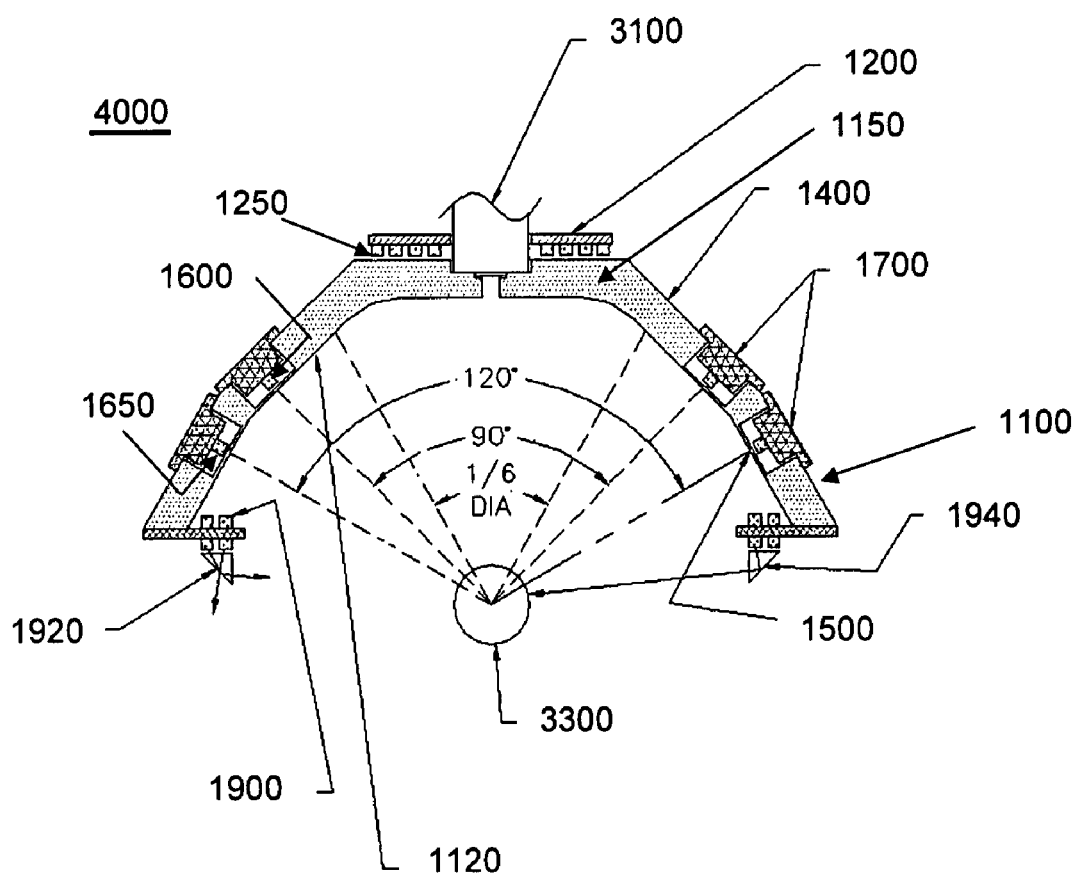
FIG. 4 is a cross-sectional view taken along plane A-A of FIG. 1 of an exemplary embodiment of a system 4000.

FIG. 4 is a cross-sectional view taken along plane A-A of FIG. 1 of an exemplary embodiment of a system 4000, which can be a "multi-sided geometry" lighting system and/or which can comprise a substantially dome-shaped diffuser 1100. To a top portion 1150 of diffuser 1100 can be secured a top mount 1200, which can secure to diffuser 1100 one or more bright field lights 1250, which can be, for example, LED's. Mounted in, above, and/or through a hole in top mount 1200 and/or within a cavity in top portion 1150 can be a lens 3100. Mounted within a hole in top portion 1150 can be an angled two way mirror 3200.

Each side portion 1400 of diffuser 1100 can include a thinned portion 1500, which can allow for minimal diffusion of low angle lighting. Securing one or more low angle lights 1600, 1650 to side portion 1400 can be a low angle light mount 1700. Securing one or more dome lights 1900 to diffuser 1100 can be a dome light mount 1800. Each of dome lights 1900 can be an LED that is directed into a beam-splitter and/or prism 1940, such as for example, a prism having three polished sides. An angled side 1920 of prism 1940 can horizontally reflect most of the light incident from the LED. A portion of the light incident from the LED can escape from prism 1940 through angled side 1920 as non-diffused light. Another potential type of prism 1940 can have the angled face 1920 of the prism textured (sandblasted). This texturing can cause the light to be partially directed horizontally and part of the light can escape out as diffused light. This can be useful for handheld barcode readers. In an exemplary implementation where this lighting would be used as an all-in-one solution for a handheld reader, this extra lighting can enable the reader to illuminate very wide barcodes. Any of lights 1250, 1600, 1650, or 1900 can be used to illuminate an inspected part 3300. An inside surface 1120 of any portion of diffuser 1100 can textured.

A first opposing pair of arrays of low angle lights 1600 located on opposing side portions 1400 of diffuser 1100 can be separated by, for example, approximately 90 degrees as measured from a cross-sectional axis of an inspected part 3300. A second opposing pair of arrays of low angle lights 1650 located on opposing side portions 1400 of diffuser 1100 can be separated by, for example, approximately 120 degrees as measured from a cross-sectional axis of an inspected part 3300. Diffuser 1100 can effectively illuminate part 3300 from up to 5 or 6 or more directions.

Figure 5:
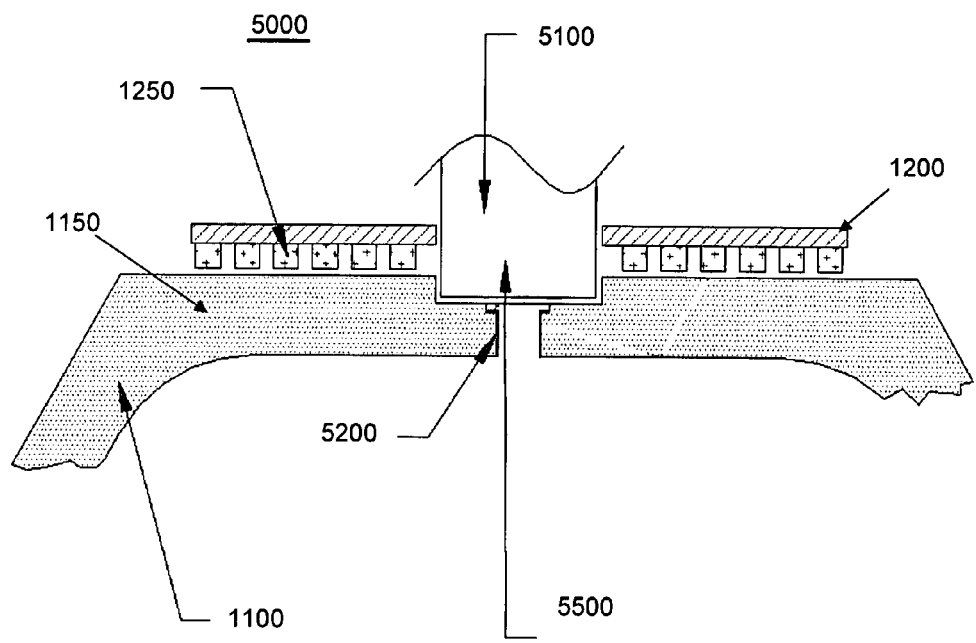
FIG. 5 is a partial cross-sectional view taken along plane A-A of FIG. 1 of an exemplary embodiment of a system 5000.

FIG. 5 is a partial cross-sectional view taken along plane A-A of FIG. 1 of an exemplary embodiment of a system 5000, which can comprise a substantially dome-shaped diffuser 1100. To a top portion 1150 of diffuser 1100 can be secured a top mount 1200, which can secure to diffuser 1100 one or more bright field lights 1250, which can be, for example, LED's. Light 5400 emitted by bright field lights 1250 can be diffused by top portion 1150 of diffuser 1100 Mounted through a hole in top mount 1200 and/or within a cavity in top portion 1150 can be a lens 5100 via which, after passing through hole 5200 in diffuser 1100, light and/or photons 5500 corresponding to an image of an inspected part can enter a camera.

Figure 6:
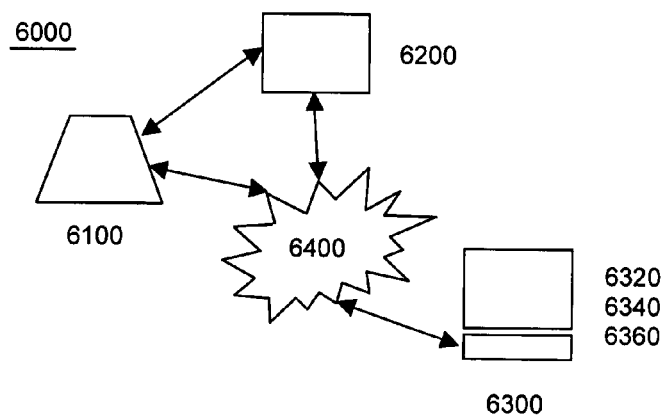
FIG. 6 is a block diagram of an exemplary embodiment of a system 6000.

FIG. 6 is a block diagram of an exemplary embodiment of a system 6000, which can comprise a diffuser sub-system 6100 the power to various lights of which can be selectively powered and/or controlled by a lighting controller 6200 and/or by an information device 6300 comprising a lighting controller 6320 that can respond to machine instructions 6340 that can be programmed via a user interface 6360. Information device 6300 can be communicatively coupled to lighting controller 6320 and/or diffuser sub-system 6100 via hardwiring and/or a network 6400.

Figure 7:
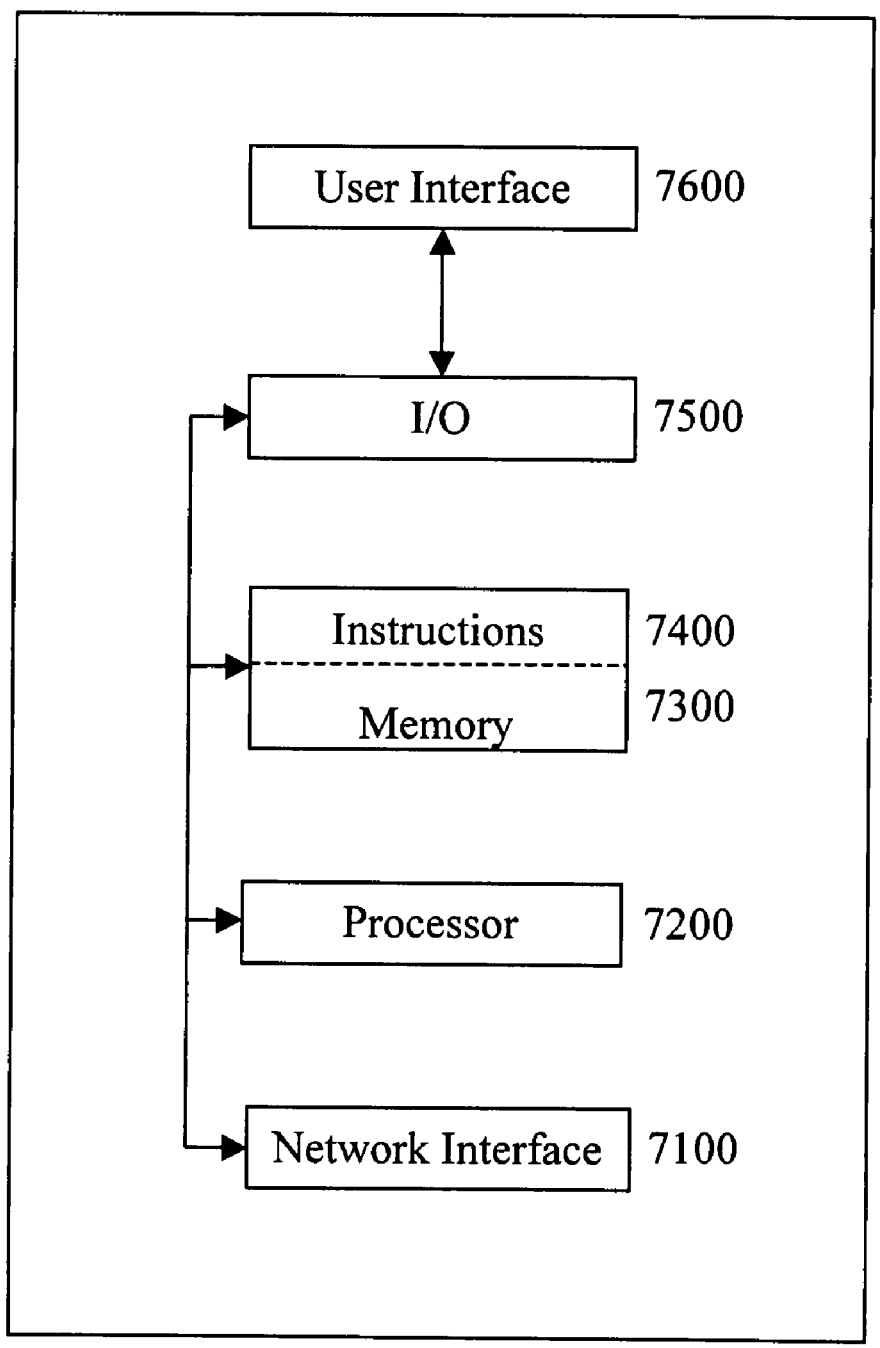
FIG. 7 is a block diagram of an exemplary embodiment of an information device 7000.

FIG. 7 is a block diagram of an exemplary embodiment of an information device 7000, which in certain operative embodiments can comprise, for example, controller 6200 and/or information device 6300 of FIG. 6. Information device 7000 can comprise any of numerous components, such as for example, one or more network interfaces 7100, one or more processors 7200, one or more memories 7300 containing instructions 7400, one or more input/output (I/O) devices 7500, and/or one or more user interfaces 7600 coupled to I/O device 7500, etc.

In certain exemplary embodiments, via one or more user interfaces 7600, such as a graphical user interface, a user can view a rendering of information related to researching, designing, modeling, creating, developing, building, manufacturing, operating, adjusting, controlling, maintaining, storing, marketing, selling, delivering, selecting, specifying, requesting, ordering, receiving, returning, rating, and/or recommending any of the systems, devices, products, services, methods, and/or information described herein.

Figure 8:
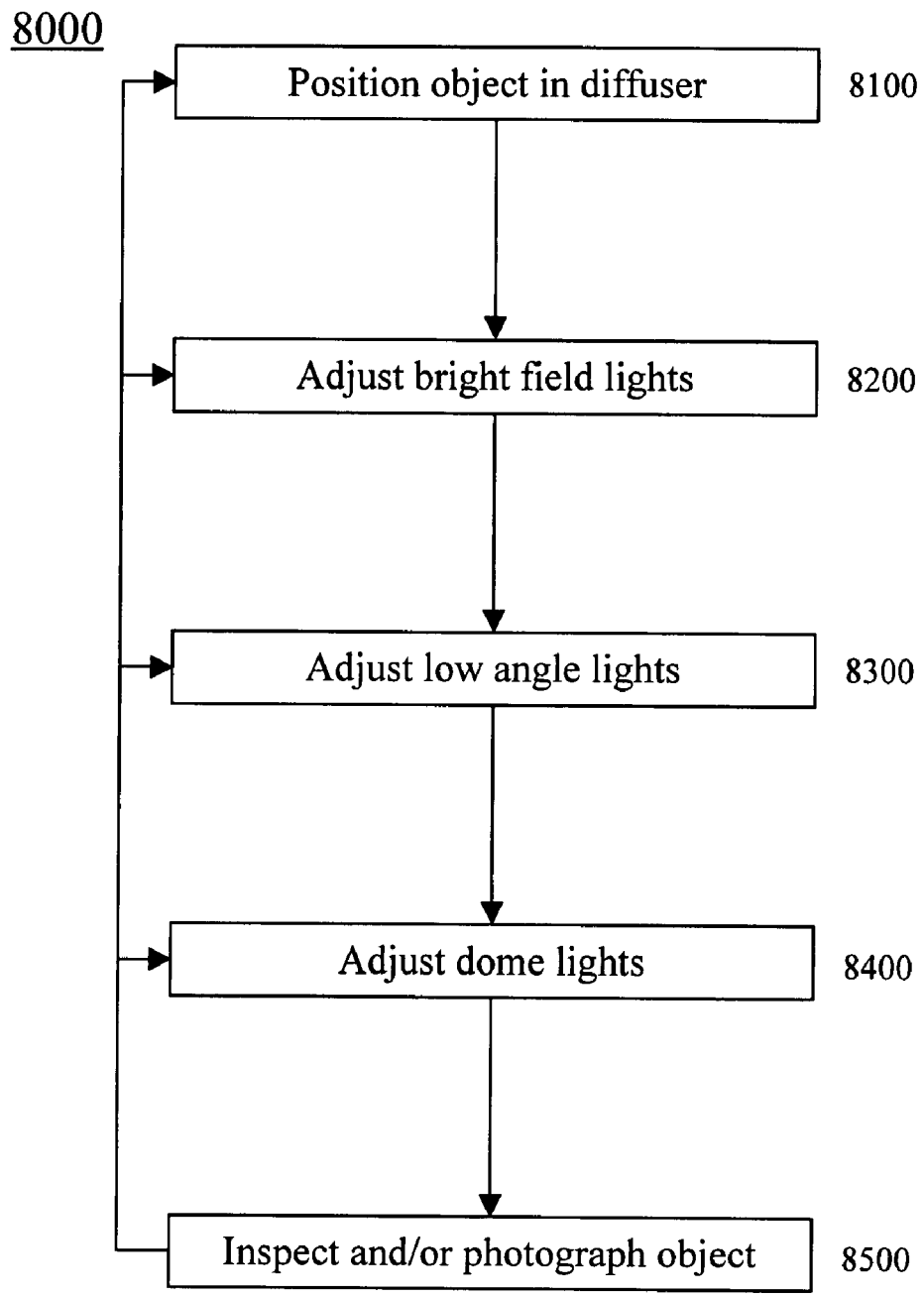
FIG. 8 is a flowchart of an exemplary embodiment of a method 8000.

FIG. 8 is a flowchart of an exemplary embodiment of a method 8000. At activity 8100, an object to be inspected, photographed, and/or illuminated can be placed and/or positionally adjusted within a substantially domed-shaped diffuser. At activity 8200, a lighting controller can be manually or automatically adjusted to cause the object to be diffusely illuminated via a least one selected set of bright field lights mounted on the diffuser. At activity 8300, a lighting controller can be manually or automatically adjusted to cause the object to be diffusely illuminated via a least one selected set of low angle lights mounted on a top portion of the diffuser. At activity 8400, a lighting controller can be manually or automatically adjusted to cause the object to be reflectively illuminated via a least one selected set of dome lights mounted on a bottom portion of the diffuser. At activity 8500, the object can be inspected, photographed, and/or an image of the object can be captured via light entering a camera via a hole in a top portion of the diffuser and a lens coupled to the camera, the lens positioned in a cavity in and/or supported by the top portion of the diffuser. Any of activities 8100-8500 can be repeated as desired. For example, the camera can cycle through a series of different lighting techniques and take a picture after each configuration change. The cycle can stop as soon as the desired image is found or it can cycle through some and/or all of the options and pick the best. Grading may happen after each image capture or at the end of all the captures.

Definitions

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
    absorb—to take in without echo, recoil, or reflection
    activity—an action, act, deed, function, step, and/or process and/or a portion thereof.
    adapted—suitable, fit, and/or capable of performing a specified function.
    adjacent—in close proximity to, near, next to, close, or contiguous; adjoining; neighboring
    allow—to provide, let do, happen, and/or permit.
    and/or—either in conjunction with or in alternative to.
    angled—slanted with respect to an adjacent object and/or reference plane.
    annular—shaped like a ring.
    apparatus—an appliance or device for a particular purpose
    at least—not less than.
    attach—to fasten, secure, couple, and/or join.
    automatic—performed via an information device in a manner essentially independent of influence and/or control by a user.

axial—located on, around, or in the direction of an axis.

axis—a straight line about which a body or geometric object rotates or can be conceived to rotate and/or a center line to which parts of a structure or body can be referred.

based—being derived from.

beam splitter—a device adapted to split or join a light beam into or from two or more beams that differ in wavelength, polarity, and/or direction.

beam splitting—a process of splitting or joining a light beam into or from two or more beams that differ in wavelength, polarity, and/or direction.

bright field—characterized by illumination at an angle such that light will be reflected into the camera lens.

camera—a device often comprising a lightproof enclosure having an aperture with a lens through which a still and/or moving image of an object is focused and recorded on a photosensitive film, plate, tape, and/or or sensor coupled to an electronic and/or optical memory device (e.g., RAM, EEPROM, flash memory, magnetic disk, optical disk, etc.)

can—is capable of, in at least some embodiments.

capture—to obtain and store.

cause—to produce an effect.

central—situated at, in, or near the center of a length.

circular—having a cross-section of a circle.

circumferential—of, at, or near the circumference; surrounding; lying along the outskirts close proximity—within approximately 0.25, 0.5, and/or 1 inches of.

co-axial—two or more objects that are located on, around, or in the direction of a common axis.

comprised—included in; a part of.

comprises—includes, but is not limited to, what follows.

comprising—including but not limited to, what follows.

cone—a solid whose surface is generated by a line passing through a fixed point and a fixed plane curve not containing the point, consisting of two equal sections joined at a vertex.

configure—to make suitable or fit for a specific use or situation.

construct—to put together the constituent parts of (something) in their proper place and order; to build; to form; and/or to make.

controller—a device and/or set of machine-readable instructions for performing one or more predetermined and/or user-defined tasks. A controller can comprise any one or a combination of hardware, firmware, and/or software. A controller can utilize mechanical, pneumatic, hydraulic, electrical, magnetic, optical, informational, chemical, and/or biological principles, signals, and/or inputs to perform the task(s). In certain embodiments, a controller can act upon information by manipulating, analyzing, modifying, converting, transmitting the information for use by an executable procedure and/or an information device, and/or routing the information to an output device. A controller can be a central processing unit, a local controller, a remote controller, parallel controllers, and/or distributed controllers, etc. The controller can be a general-purpose microcontroller, such the Pentium IV series of microprocessor manufactured by the Intel Corporation of Santa Clara, Calif., and/or the HC08 series from Motorola of Schaumburg, Ill. In another embodiment, the controller can be an Application Specific Integrated Circuit (ASIC) or a Field Programmable Gate Array (FPGA) that has been designed to implement in its hardware and/or firmware at least a part of an embodiment disclosed herein.

convey—to transmit, transport, guide, and/or carry.

couple—to join, connect, and/or link two things together.

cylindrical—of, relating to, and/or having the shape of a cylinder, especially of a circular cylinder.

data—distinct pieces of information, usually formatted in a special or predetermined way and/or organized to express concepts.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

define—to establish the meaning, relationship, outline, form, and/or structure of; and/or to precisely and/or distinctly describe and/or specify.

determine—to obtain, calculate, decide, deduce, and/or ascertain.

device—a machine, manufacture, and/or collection thereof.

diffuse—to spread or scatter.

diffuser—a substantially translucent structure adapted to expand the diameter of a light source and/or reduce the effects of focused or collimated lighting.

direction—a spatial relation between something and a course along which it points and/or moves; a distance independent relationship between two points in space that specifies the position of either with respect to the other; and/or a relationship by which the alignment and/or orientation of any position with respect to any other position is established.

dome-shaped—having the shape and/or form of a dome and/or a structure having a circular, polygonal, or elliptical base and a very generally hemispherical or semi-spherical shape.

each—every one of a group considered individually.

enable—to render capable for a task.

encircle—to surround at least a portion of, in at least one plane.

end—an extremity and its vicinity of something that has length; a terminus.

energize—to apply electricity to.

extending—located, placed, and/or stretched lengthwise.

face—the most significant or prominent surface of an object.

fit—to be of the right size or shape, as a garment for the wearer or any object or part for a thing to which it is applied formed—constructed.

from—used to indicate a source.

further—in addition.

generate—to create, produce, give rise to, and/or bring into existence.

hole—a hollowed place in an object.

illuminate—to light and/or cause light to be incident thereon.

image—an at least two-dimensional representation of an entity and/or phenomenon. Multiple images can be presented in a predetermined and timed sequence to recreate and/or produce an appearance of movement.

incident—falling or striking on something include—comprise information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as a Treo-like device), messaging service (e.g., Blackberry) receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

inspect—to review.

interior—being within; inside of anything; internal; inner; further toward a center.

into—to a condition, state, or form of.

lens—a piece of transparent substance, usually glass, having two opposite surfaces either both curved or one curved and one plane, used in an optical device for changing the convergence and/or focal point of light rays; an optical device with approximate axial symmetry that transmits light, refracts light, and is adapted to cause the light to concentrate and/or diverge.

light—electromagnetic radiation of any wavelength.

light emitting diode (LED)—a semiconductor device that emits light responsive to an applied electrical conducting current.

lighting—an illuminating agent or source.

location—a place.

longitudinal—of and/or relating to a length; placed and/or running lengthwise.

low angle light—a light that illuminates in such a manner as to cause the light to be reflected away from a camera lens machine—a device and/or vehicle adapted to perform at least one task.

machine instructions—directions adapted to cause a machine, such as an information device, to perform one or more particular activities, operations, or functions. The directions, which can sometimes form an entity called a "processor", "kernel", "operating system", "program", "application", "utility", "subroutine", "script", "macro", "file", "project", "module", "library", "class", and/or "object", etc., can be embodied as machine code, source code, object code, compiled code, assembled code, interpretable code, and/or executable code, etc., in hardware, firmware, and/or software.

machine readable medium—a physical structure from which a machine can obtain data and/or information. Examples include a memory, punch cards, etc.

may—is allowed and/or permitted to, in at least some embodiments.

memory device—an apparatus capable of storing analog or digital information, such as instructions and/or data. Examples include a non-volatile memory, volatile memory, Random Access Memory, RAM, Read Only Memory, ROM, flash memory, magnetic media, a hard disk, a floppy disk, a magnetic tape, an optical media, an optical disk, a compact disk, a CD, a digital versatile disk, a DVD, and/or a raid array, etc. The memory device can be coupled to a processor and/or can store instructions adapted to be executed by processor, such as according to an embodiment disclosed herein.

method—a process, procedure, and/or collection of related activities for accomplishing something.

minimal—at a lowest level.

mirror—a reflecting surface.

mount—(n) that upon which a thing is attached. (v) to couple, fix, and/or attach on and/or to something.

network—a communicatively coupled plurality of nodes. A network can be and/or utilize any of a wide variety of sub-networks, such as a circuit switched, public-switched, packet switched, data, telephone, telecommunications, video distribution, cable, terrestrial, broadcast, satellite, broadband, corporate, global, national, regional, wide area, backbone, packet-switched TCP/IP, Fast Ethernet, Token Ring, public Internet, private, ATM, multi-domain, and/or multi-zone sub-network, one or more Internet service providers, and/or one or more information devices, such as a switch, router, and/or gateway not directly connected to a local area network, etc.

network interface—any device, system, or subsystem capable of coupling an information device to a network. For example, a network interface can be a telephone, cellular phone, cellular modem, telephone data modem, fax modem, wireless transceiver, ethernet card, cable modem, digital subscriber line interface, bridge, hub, router, or other similar device.

non—not.

object—a physical thing.

outer—farther than another from the center and/or middle.

parallel—of, relating to, or designating lines, curves, planes, and/or or surfaces everywhere equidistant and/or an arrangement of components in an electrical circuit that splits an electrical current into two or more paths.

perpendicular—intersecting at or forming substantially right angles; and/or substantially at a right angle with respect to an axis.

plastic—any of a group of synthetic or natural organic materials that may be shaped when soft and then hardened, including many types of resins, resinoids, polymers, cellulose derivatives, casein materials, and proteins: used in place of other materials, as glass, wood, and metals, in construction and decoration, for making many articles, as coatings, and, drawn into filaments, for weaving.

plurality—the state of being plural and/or more than one.

portion—a part, component, section, percentage, ratio, and/or quantity that is less than a larger whole. Can be visually, physically, and/or virtually distinguishable and/or non-distinguishable.

position—to put in place or position.

power—energy, a measure of energy and/or work, and/or a rate at which work is done, expressed as the amount of work per unit time and commonly measured in units such as watt and horsepower.

predefined—specified, determined, and/or established in advance.

predetermined—established in advance.

processor—a device and/or set of machine-readable instructions for performing one or more predetermined tasks. A processor can comprise any one or a combination of hardware, firmware, and/or software. A processor can utilize mechanical, pneumatic, hydraulic, electrical, magnetic, optical, informational, chemical, and/or biological principles, signals, and/or inputs to perform the task(s). In certain embodiments, a processor can act upon information by manipulating, analyzing, modifying, converting, transmitting the information for use by an executable procedure and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium IV series of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein.

provide—to furnish, supply, give, convey, send, and/or make available.

proximity—the state, quality, sense, and/or fact of being near and/or next; the closeness of one thing to another.

pyramid—a solid having a polygonal base and triangular sides that meet in a point.

reach—to arrive at.

receive—to gather, take, acquire, obtain, accept, get, and/or have bestowed upon.

reflect—to cast back incident light from a surface.

region—a continuous part of a surface.

render—to make perceptible to a human, for example as data, commands, text, graphics, audio, video, animation, and/or hyperlinks, etc., such as via any visual, audio, and/or haptic means, such as via a display, monitor, electric paper, ocular implant, cochlear implant, speaker, etc.

repeatedly—again and again; repetitively.

requirement—a demand, need, and/or request.

response—a reaction to an influence and/or impetus.

said—when used in a system or device claim, an article indicating a subsequent claim term that has been previously introduced.

second—immediately following an initial item in an ordering.

select—to make a choice or selection from alternatives.

selectively—via choice.

set—a related plurality of predetermined elements; and/or one or more distinct items and/or entities having a specific common property or properties.

shape—a characteristic surface, outline, and/or contour of an entity.

side—a surface bounding a solid object.

signal—information, such as machine instructions for activities, encoded as automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc. Depending on the context, a signal can be synchronous, asynchronous, hard real-time, soft real-time, non-real time, continuously generated, continuously varying, analog, discretely generated, discretely varying, quantized, digital, continuously measured, and/or discretely measured, etc.

source—an original transmitter and/or a point at which something originates, springs into being, and/or from which it derives and/or is obtained.

store—to place, hold, and/or retain data, typically in a memory.

strike—to come upon or reach in traveling.

substantially—to a considerable, large, and/or great, but not necessarily whole and/or entire, extent and/or degree.

support—to bear the weight of, especially from below.

surface—an outer boundary of an object or a material layer constituting or resembling such a boundary.

surround—to encircle, enclose, and/or confine on one or more sides.

system—a collection of mechanisms, devices, data, and/or instructions, the collection designed to perform one or more specific functions.

textured—not smooth.

thereon—on or upon this, that, or it.

thinned—having a cross-section at that location that is substantially smaller than a cross-section taken at an adjacent location.

through—in one side and out the opposite or another side of, across, among, and/or between.

top—an uppermost point.

transmit—to send as a signal, provide, furnish, and/or supply.

transparent—clear; characterized by conveying incident light without reflecting or absorbing a substantial portion of that light; and/or having the property of transmitting rays of light through its substance so that bodies situated beyond or behind can be distinctly seen.

travel—to go and/or appear to go from one place to another; and/or to pass and/or be transmitted.

truncated—of a geometric figure or solid) having the apex, vertex, or end cut off by a plane.

tube—an elongate member having a longitudinal axis and defining a longitudinal cross-section resembling any closed shape such as, for example, a circle, a non-circle such as an oval (which generally can include a shape that is substantially in the form of an obround, ellipse, limaçon, cardioid, cartesian oval, and/or Cassini oval, etc), and/or a polygon such as a triangle, rectangle, square, hexagon, the shape of the letter "D", the shape of the letter "P", etc. Thus, a right circular cylinder is one form of a tube, an elliptic cylinder is another form of a tube having an elliptical longitudinal cross-section, and a generalized cylinder is yet another form of a tube.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

via—by way of and/or utilizing.

wall—a partition, structure, and/or mass that serves to enclose, divide, separate, segregate, define, and/or protect a volume and/or to support a floor, ceiling, and/or another wall.

wherein—in regard to which; and; and/or in addition to.

within—inside.

zone—and volume and/or region.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, abstract, drawing figure, etc.) of this application, unless clearly specified to the contrary, such as via an explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, performed by multiple entities, and/or performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a U.S. patent, U.S. patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

Accordingly, every portion (e.g., title, field, background, summary, abstract, drawing figure, etc.) of this application, other than the claims themselves, is to be regarded as illustrative in nature, and not as restrictive.

What is claimed is:

1. A system for illuminating an object, the system comprising:
    a substantially dome-shaped diffuser, said diffuser including a camera lens hole positioned along an optical axis of the diffuser in a top portion of said diffuser, said diffuser including mounts in a side portion thereof to receive at least one set of low angle lights; and
    a plurality of bright field lights mounted on said diffuser substantially adjacent said camera lens hole and pointing substantially parallel to the optical axis, such that the plurality of bright field lights direct light toward the object through the portion of the diffuser adjacent to the camera lens hole.

2. The system of claim 1, wherein:
    said diffuser is formed substantially in the shape of a truncated 4-sided pyramid.

3. The system of claim 1, wherein:
    said diffuser is formed substantially in the shape of a truncated circular cone.

4. The system of claim 1, wherein:
each of said bright field lights comprises at least one LED.

5. The system of claim 1, further comprising:
said at least one set of low angle lights mounted on said diffuser.

6. The system of claim 1, further comprising:
said at least one set of low angle lights mounted on said diffuser, each low angle light in said set mounted at a location on said diffuser adjacent a thinned diffuser wall.

7. The system of claim 1, further comprising:
said a least one set of low angle lights mounted on said diffuser, each of said low angle lights comprised of at least one LED.

8. The system of claim 1, further comprising:
a camera lens mounted co-axially with said camera lens hole, said camera lens attached to a camera.

9. The system of claim 1, wherein:
said diffuser is textured and diffusely reflective.

10. The system of claim 1, further comprising a plurality of dome lights mounted to said diffuser to substantially face at least a portion of said diffuser.

11. The system of claim 10, further comprising a lighting controller that can selectively energize at least one of:
a low angle light from the set of low angle lights;
a bright field light from the plurality of bright field lights; and
a dome light from the plurality of dome lights.

12. The system of claim 1, further comprising a lighting controller to selectively energize at least one of:
a low angle light from said set of low angle lights; and
a bright field light from said plurality of bright field lights.

13. The system of claim 1, further comprising a lighting controller to, in response to machine instructions, power at least one of:
a low angle light from said set of low angle lights; and
a bright field light from said plurality of bright field lights.

14. The system of claim 1 wherein the set of low angle lights comprise at least four lights that can be selectively energized to illuminate from one direction, two directions, or four directions.

15. An automatic lighting system for camera based inspections, comprising:
a diffuser;
a camera lens positioned in a camera lens hole on the diffuser, the camera lens having an optical axis;
a plurality of bright field LED lights provided on the diffuser substantially adjacent the camera lens and pointing substantially parallel to the optical axis, such that the plurality of bright field LED lights direct light toward an object through the portion of the diffuser adjacent to the camera lens hole; and
at least one set of low angle lights mounted to a side portion of the diffuser, wherein the diffuser is shaped to provide light at angles that enable a plurality of lighting requirements for camera-based inspections.

16. The system of claim 15, further comprising:
a low angle LED mount provided on a thinned portion of the diffuser, the thinned portion of the diffuser providing minimal diffusion of low angle lights.

17. The system of claim 15, further comprising:
dome LEDs provided on an end portion of the diffuser.

18. The system of claim 15, further comprising:
dome LEDs provided on an end portion of the diffuser, wherein the dome LEDs include a textured surface for beam splitting.

19. The system of claim 15, further comprising a lighting controller to selectively energize at least one of:
a low angle light from said set of low angle lights; and
a bright field light from said plurality of bright field lights.

20. The system of claim 15 wherein the set of low angle lights comprise at least four lights that can be selectively energized to illuminate from one direction, two directions, or four directions.

21. A method comprising:
illuminating an object via:
at least one set of low angle lights mounted on a side portion of a substantially domed-shaped diffuser, the diffuser defining a camera lens hole positioned along an optical axis of the diffuser in a top portion of the diffuser to allow light reflected from the object to reach a camera lens; and
a plurality of bright field lights mounted on the diffuser substantially adjacent to the camera lens hole and pointing substantially parallel to the optical axis, such that the plurality of bright field lights direct light toward the object through the portion of the diffuser adjacent to the camera lens hole.

22. The method of claim 21 wherein the diffuser is formed substantially in the shape of a truncated 4-sided pyramid or substantially in the shape of a truncated circular cone.

23. The method of claim 21 wherein the diffuser is textured and diffusely reflective.

24. The method of claim 21, further comprising positioning the diffuser and the object relative to each other to align light reflected from the object into the camera lens hole of the diffuser.

25. The method of claim 21, further comprising selectively or automatically de-energizing at least one of:
a low angle light from the at least one set of low angle lights; and
a bright field light from the plurality of bright field lights.

26. The method of claim 21, further comprising illuminating the object via at least one set of dome lights mounted to the diffuser to direct light toward an interior surface of said diffuser.

27. The method of claim 26, further comprising selectively or automatically energizing at least one of:
a low angle light from the set of low angle lights;
a bright field light from the plurality of bright field lights; and
a dome light from the plurality of dome lights.

28. The method of claim 21 wherein the set of low angle lights comprise at least four lights, and further comprising selectively energizing the low angle lights to illuminate from one direction, two directions, or four directions.

29. The method of claim 21 wherein each low angle light in the set of low angle lights is mounted at a location on the diffuser adjacent a thinned diffuser wall.

30. The method of claim 21 wherein the plurality of bright field lights substantially encircle the camera lens hole.

31. The method of claim 21, further comprising coupling the camera lens to the diffuser.

32. The method of claim 21, further comprising capturing an image of the object via a camera coupled to the camera lens.

33. The method of claim 21 wherein the camera lens is mounted substantially co-axially with the camera lens hole, the camera lens attached to a camera.

34. A method comprising:

automatically illuminating an object via at least two lighting sources selected from:

- a bright field light mounted on a top portion of a substantially domed-shaped diffuser substantially adjacent to a camera lens hole positioned along an optical axis of the diffuser in the top portion of the diffuser, wherein the bright field light points substantially parallel to the optical axis such that the bright field light directs light toward the object through the portion of the diffuser adjacent to the camera lens hole, wherein the camera lens hole allows light reflected from the object to reach a camera lens,
- a low angle light mounted on a side portion of the diffuser and oriented to substantially face an interior zone of the diffuser, and
- a dome light mounted to the diffuser to direct light toward an interior surface of the diffuser.

* * * * *